United States Patent [19]

Tachon et al.

[11] Patent Number: 5,505,959
[45] Date of Patent: Apr. 9, 1996

[54] PHARMACEUTICAL COMPOSITION IN GEL FORM IN A DISPENSING PACKAGE

[75] Inventors: Pierre Tachon, Cugy, Switzerland; Beatrice Vagneur, Angers, France; Jean-Louis Viret, Brent, Switzerland

[73] Assignee: Nestec S.A., Vevey, Switzerland

[21] Appl. No.: 220,826

[22] Filed: Mar. 31, 1994

Related U.S. Application Data

[63] Continuation of Ser. No. 756,357, Sep. 9, 1991, Pat. No. 5,300,302.

[30] Foreign Application Priority Data

Oct. 4, 1990 [EP] European Pat. Off. ............ 90118920

[51] Int. Cl.$^6$ ................ A61K 9/10; A61K 9/50; A61K 9/127
[52] U.S. Cl. ................ 424/450; 424/43; 424/45; 424/451; 424/489; 424/487; 514/944
[58] Field of Search ............... 424/486, 487, 424/43, 45, 450, 451, 489, 484; 514/944

[56] References Cited

U.S. PATENT DOCUMENTS

| | | | |
|---|---|---|---|
| Re. 32,969 | 6/1989 | Trager | 424/81 |
| 3,767,784 | 10/1973 | Gluck | 424/28 |
| 4,136,177 | 1/1979 | Lin et al. | 424/211 |
| 4,155,741 | 5/1979 | Scher et al. | 71/65 |
| 4,305,933 | 12/1981 | Wiczer | 424/180 |
| 4,424,055 | 1/1984 | Herman | 604/36 |
| 4,427,681 | 1/1984 | Munshi | 424/260 |
| 4,576,645 | 3/1986 | Ravel et al. | 106/125 |
| 4,708,834 | 11/1987 | Cohen et al. | 264/4.3 |
| 4,994,277 | 2/1991 | Higham et al. | 424/443 |
| 5,008,117 | 4/1991 | Calanchi et al. | 424/494 |
| 5,215,739 | 6/1993 | Kamishita et al. | 424/45 |
| 5,300,302 | 4/1994 | Tachon et al. | 424/488 |

FOREIGN PATENT DOCUMENTS 0379147  7/1990  European Pat. Off. .

*Primary Examiner*—Thurman K. Page
*Assistant Examiner*—James M. Spear
*Attorney, Agent, or Firm*—Vogt & O'Donnell

[57] ABSTRACT

A pharmaceutical delivery system includes a dispenser pack containing a pharmaceutical composition. The composition includes a pharmaceutical active principle homogeneously distributed in a water-dispersible gel excipient containing an acrylamide or acrylamidine gelling agent.

17 Claims, No Drawings

PHARMACEUTICAL COMPOSITION IN GEL FORM IN A DISPENSING PACKAGE

CROSS REFERENCE TO RELATED APPLICATION

This application is a continuing application of application Ser. No. 07/756,357, filed Sep. 9, 1991, now U.S. Pat. No. 5,300,302.

BACKGROUND OF THE INVENTION

This invention relates to a pharmaceutical composition in a package in which the active principle is presented in a gel-form excipient.

For several centuries, medicaments have been orally administered as syrups from bottles or in the form of tablets or capsules.

Such presentations are easy to absorb and enable the active substances to be preserved. However, syrups are attended by certain disadvantages, including for example the following:

- the high sugar content can be troublesome, for example in diabetics,
- the therapeutic dose is not directly accessible, necessitating the use of a measure, for example a spoon, so that the dose administered is not exact,
- the method of formulation does not lend itself to the administration of a therapeutic dose in babies and nursing infants who may refuse to take the spoon or may upset the syrup, and
- children can take the entire contents of the bottle all at once with the attendant risk of intoxication.

In addition, tablets and capsules are unsuitable for certain patients, for example young children or geriatrics having problems with swallowing.

EP-A-0 379 147 relates to an extrudable gel as a support for an active principle which can be distributed in a pack equipped with a metering pump. The gel in question contains the active principle in solution and comprises a gelling agent based on an algal extract, for example a carrageenate. The fact that the active principle has to be in solution dictates a low concentration with the result that, in the example provided, the administration of a daily therapeutic dose means that the pump has to be depressed 12 to 60 times on 3 or 4 occasions, consuming the product volume of an entire pack, which is an enormous disadvantage. This drawback cannot be rectified simply by increasing the concentration of the active principle because this would adversely affect the stability of the gel, the mass being viscous and non-gelled and the active principle non-solubilized, and its organoleptic acceptability.

SUMMARY OF THE INVENTION

The problem addressed by the present invention is to provide a formulation in gel form in a dispenser with an element for metering active principles normally in syrup, tablets or capsule form which does not have any of the disadvantages of the known dispensable gel. The invention is concerned in this regard with convenience, hygiene and safety of use, particularly in children, babies and nursing infants and in any patients having problems with swallowing. Another particular objective of the invention is to provide for administration to diabetics.

Added to the foregoing objectives is the ability to deliver a therapeutic dose of low volume by one or two depressions of the dispenser which, in some cases, requires a high concentration of active principle in suspension in the gel which, nevertheless, has to show the properties of rheological stability and organoleptic acceptability compatible with the method of distribution.

Applicants have found a convenient, hygienic and safe formulation for the active principles normally administered in syrup form which satisfies the requirements stated above.

The present invention provides a process for preparing a pharmaceutical composition for being packaged in a metering dispenser characterized in that a pharmaceutical active principle is contained in a gel. The composition is prepared by adding a gelling agent to an aqueous medium containing a pharmaceutical active principle and stirring to form a gel. Prior to gelling, the active principle may be contained in the aqueous medium in solution or in a solid form. Depending upon the active principle, the active principle may be solubilized with water or with a solvent inert to the constituents of the matrix gel, or it may be encapsulated or coated for being contained in the aqueous medium and hence, in the gel. A preservative, a flavoring, a sweetening agent and a colorant may be mixed with water and the active principle to prepare the aqueous medium to be gelled, after which the gelling agent is added with stirring to the mixture to form the gel.

The composition is prepared further for dispensing by packing the gel in a dispenser pack having a metering pump for dispensing metered amounts of the gel.

Thus, the pharmaceutical composition according to the invention is characterized in that the active principle is homogeneously distributed in a pseudoplastic water-dispersible gel which does not run during dispensing and which is organoleptically acceptable. The gel may be dispersed in a predetermined volume from a dispenser pack having a metering pump. The gel may be contained in a dispenser pack having an internal volume of 20 to 150 ml and which is provided with a metering compartment not exceeding 5 ml in volume and with a metering pump designed to dispense a therapeutic dose in one or two depressions per therapeutic dose and in that the contents of the dispenser are sufficient for at least 5 days' treatment.

DETAILED DESCRIPTION OF THE INVENTION

According to the invention, any active principle typically administered orally in syrup, tablet or capsule form may be formulated as a gel for dispensing.

For example, the following active principles and pharmaceutically acceptable salts thereof may be used in the following doses.

The names used for the active principles are the common international names.

The doses are expressed in mg per therapeutic dose. One dose may sometimes correspond to one depression of the dispenser, i.e 2 ml, and sometimes to two depressions, i.e., 4 ml.

The therapeutic dose may be repeated 2 to 5 times a day according to the prescription and the type of treatment.

| Oral antacids as gastrointestinal or anti-ulcer treatments: | |
|---|---|
| Aluminium or magnesium phosphates | 500–600 mg/4 ml |
| Aluminium hydroxide and magnesium hydroxide | 400 mg/ 400 mg/4 ml |
| Sucralfate | 500–1000 mg/4 ml |
| Antidiarrhoeics: | |
| Insoluble polyphenols of carob | 500 mg/2 ml |
| Loperamide | 1–4 mg/2 ml |
| Anti H1 antihistaminics: | |
| Carbinoxamine | 2 mg/2 ml |
| Acrivastine | 1–10 mg/2 ml |
| Triprolidine | 1–100 mg/2 ml |
| Anti-emetics: | |
| Dimenhydrinate | 10–150 mg/2 ml |
| Antitussives: | |
| Cloperastine | 4–10 mg/2 ml |
| Codeine | 10–30 mg/2 ml |
| Dextromethorphan | 5–30 mg/2 ml |
| Anti-inflammatories: | |
| Ibuprofen | 100–600 mg/4 ml |
| Flurbiprofen | 25–300 mg/2–4 ml |
| Diclofenac | 10–150 mg/2–4 ml |
| Analgesics/antipyretics: | |
| Dextropropoxyphene | 30–70 mg/2 ml |
| Paracetamol | 125–500 mg/2–4 ml |
| Aspirin (salt) | 50–500 mg/2–4 ml |
| Bronchial mucomodifiers: | |
| Acetylcysteine (stabilized) | 100–600 mg/4 ml |
| Carbocysteine | 100–750 mg/2–4 ml |
| Guaiphenesin | 50–200 mg/2–4 ml |
| Ambroxol | 3–30 mg/2–4 ml |
| Antispasmodics: | |
| Phloroglucinol | 50–150 mg/2–4 ml |
| Respiratory analeptics/antiasthmatics: | |
| Theophylline | 50–200 mg/2–4 ml |
| Systemic alpha-sympathomimetics: | |
| Pseudoephedrine | 25–120 mg/2–4 ml |
| Vitamins and/or oligoelements in vitamin complex form | 50–350 mg/2–4 ml |
| Laxatives: | |
| Docusate | 20–200 mg/2–4 ml |
| Bisacodyl | 5–30 mg/2 ml |

It is of course possible to use associations of compatible active principles. The following list is given by way of example:

| Alpha-sympathomimetic and anti H1 antihistaminic: | |
|---|---|
| Pseudoephedrine and | 25–120 mg/ |
| Triprolidine | 1–100 mg/2–4 ml |
| Antihistaminic and opiated antitussive: | |
| Pseudoephedrine and | 25–120 mg/ |
| Dextromethorphan | 5–30 mg/2–4 ml |
| Alpha-sympathomimetic and bronchial mucomodifier: | |
| Pseudoephedrine and | 25–120 mg/ |
| Guaiphenesin | 50–120 mg/2–4 ml |
| Alpha-sympathomimetic, antitussive and antihistaminic: | |
| Pseudoephedrine, | 25–120 mg/ |
| Dextromethorphan and | 5–30 mg/ |
| Triprolidine | 1–100 mg/2–4 ml |
| Alpha-sympathomimetic, mucomodifier and antihistaminic: | |
| Pseudoephedrine, | 25–120 mg/ |
| Guaiphenesin and | 50–200 mg/ |
| Triprolidine | 1–100 mg/2–4 ml |
| Alpha-sympathomimetic, antihistaminic and opiated antitussive: | |
| Pseudoephedrine, | 25–120 mg/ |
| Triprolidine and | 1–100 mg/ |
| Codeine phosphate | 3–50 mg/2–4 ml |
| Antihistaminic and opiated antitussive: | |
| Triprolidine and | 1–100 mg/ |
| Dextromethorphan | 5–30 mg/2–4 ml |
| Antihistaminic and analgesic/antipyretic: | |
| Triprolidine and | 1–100 mg/ |
| Paracetamol | 125–250 mg/2–4 ml |
| Triprolidine and | 1–100 mg/ |
| Ibuprofen | 125–250 mg/2–4 ml |
| Alpha-sympathomimetic and analgesic/antipyretic: | |
| Pseudoephedrine and | 10–120 mg/ |
| Paracetamol | 125–250 mg/2–4 ml |
| Pseudoephedrine and | 10–120 mg/ |
| Ibuprofen | 125–250 mg/2–4 ml |
| Antihistaminic and alpha-sympathomimetic: | |
| Acrivastine and | 1–10 mg/ |
| Pseudoephedrine | 10–120 mg/2–4 ml |
| Antihistaminic, alpha-sympathomimetic and analgesic/antipyretic: | |
| Acrivastine, | 1–10 mg/ |
| Pseudoephedrine and | 10–120 mg/ |
| Paracetamol | 125–250 mg/2–4 ml |
| Antihistaminic, alpha-sympathomimetic and opiated antitussive: | |
| Acrivastine, | 1–10 mg/ |
| Pseudoephedrine and | 10–120 mg/ |
| Dextromethorphan | 5–30 mg/2–4 ml |
| Antihistaminic, alpha-sympathomimetic and mucomodifier: | |
| Acrivastine, | 1–10 mg/ |
| Pseudoephedrine and | 10–120 mg/ |
| Guaiphenesin | 50–250 mg/2–4 ml |
| Antihistaminic, alpha-sympathomimetic and anti-inflammatory (aryl carboxylic derivatives): | |
| Acrivastine, | 1–10 mg/ |
| Pseudoephedrine and | 10–120 mg/ |
| Ibuprofen | 50–600 mg/2–4 ml |

A suitable dispenser pack comprises a metering compartment and a metering pump enabling an exact volume of medicament predetermined by the metering compartment to be dispensed by application of pressure to an actuating head of the pump. Dispensers of the type in question are widely used in the cosmetics field, for example for applying creams. For example, they may be formed by a cylindrical body of plastic, aluminium or glass filled with product and closed at its base by a plunger and equipped at its head with a metering pump which, actuated by pressure applied to the head, draws up a dose of product and then discharges it through a nozzle formed in the head.

Alternatively, the body may comprise a flexible membrane in the form of a finger containing the product and a propellant gas which applies a pressure to the membrane so that a dose of product is discharged through the nozzle when a pressure applied to the head opens an inlet valve for the product.

The dispenser pack may contain 20 to 150 ml and preferably 20 to 100 ml gel.

The metering compartment preferably has a useful volume of approximately 2 ml corresponding to the unit dose to be dispensed.

The excipient is in the form of a pseudoplastic and more or less thixotropic water-dispersible gel. The required pseudoplasticity corresponds to a resistance of the gel which is plastic up to a certain shear limit, but breaks beyond that limit. Thixotropy is understood to be the property which the gel has of becoming less viscous when subjected to constant shearing (constant friction in the metering element during dispensing) and returning to its initial structure after removal of the shear force and standing for a sufficient time. The consistency of the gel should be such that it can be pumped, is sufficiently deformable for exactly filling the volume of the metering compartment without becoming stringy and can be discharged from the compartment and broken to form an extrudable dose without running during dispensing. In addition, this property of pseudoplasicity enables the gel to be deposited onto a support, for example a spoon, and to adhere sufficiently to the support without dropping, even when the spoon is turned upside down. In addition, because the gel is dispersible in water, it does not adhere to the mucosa, but at the same time is not destructured in the mouth so that it is easy to swallow.

The gel forms a matrix which should be as inert as possible with respect to the active principle and its bioavailability. The rheological properties defined above may be obtained by means of gelling agents, optionally in combination with suitable flow modifiers which impart these properties to the matrix and maintain them as a function of time. The gelling agents may be of natural origin, for example xanthan gums or dextran obtained by fermentation, vegetable origin, for example celluloses and derivatives of methyl cellulose, hydroxyethyl cellulose, hydroxypropyl cellulose, hydroxypropyl methyl cellulose and carboxymethyl cellulose, starches and dextrins, or synthetic origin, for example carbomers, acrylamides, acrylamidines, polyglycols, esters of polyols with fatty acids.

In certain cases, it may be useful to modify the rheology of some of these gelling agents, for example to modify and, in particular, enhance the thixotropic properties of the matrix, for example by addition of magnesium aluminosilicate to a cellulose.

The pseudoplasticity of the matrix must of course be adapted to the design of the dispenser and, in particular, to the type of metering element, for example a piston or bellows pump.

The gelling agent makes up 0.2 to 5% by weight of the composition.

If therapeutically necessary, the active principle may be present in the matrix gel in the form of a homogeneous solution, for example when it is highly soluble in water or when the therapeutic dose is small, or in the form of a dispersion. In certain cases, the active principle has to undergo certain treatments before it is dispersed in the matrix gel with a view to increasing its concentration or to masking its taste, for example in cases where it is bitter. Thus, the active principle may be solubilized in a solvent which is inert to the constituents of the matrix gel and then emulsified, for example by dissolution in a lipid followed by formation of an oil-in-water emulsion, i.e., by dispersing the oil droplets in the gel. The active principle may be dispersed in the form of microcrystals. It may be encapsulated in an open newtonian system, for example a microsponge, such as for example a micronized, porous solid adsorbate based on aluminium trisilicate, or in an open brownian system, for example beta-cyclodextrin, or in a closed newtonian matrix system, for example of microspheres, or vesicularsystem, for example of microcapsules, or in a closed brownian matrix system, for example of nanocapsules, or vesicular system, for example of synthetic nanocapsules or liposomes. The active principle may also be coated by coacervation, co-precipitation or interfacial polymerization. These techniques may be carried out in a fluidized air bed, by drying, by spraying or by evaporation of non-miscible solvents in emulsion.

The composition may also contain sugars or sweetening agents, preservatives, solubilizers, flavourings and colourants. If the active principle is bitter, its bitterness may be masked by addition of sweetening agents with the proviso that the sweetening agent in question does not significantly affect the rheological properties of the matrix gel.

Suitable sweetening agents include, for example, glucose and its polymers, preferably sucrose in a concentration of 20 to 30% by weight, based on the composition as a whole, the sweetening agent being used in a sufficient quantity (more than 20%) to at least partly mask the bitter taste. In a concentration above 30%, sucrose would impart stringing properties to the gel which would lose its pseudoplasticity. Other sweetening agents may be used to enhance the sweetening power of the sucrose, for example sodium cyclamate and/or preferably ammonium glycyrrhizinate in a concentration of 0.01 to 0.6% by weight, based on the composition as a whole.

In one particular embodiment of the pharmaceutical composition providing for administration of the active principles to diabetics, the sweetening agent may be, for example, aspartame in a concentration of 0.03 to 0.6% by weight, based on the composition as a whole. A solubilizer for the active principle, for example glycerol, may be added to the composition.

In one particular embodiment of the process according to the invention, the active principle is encapsulated with a view to modifying the organoleptic characteristics of the composition before it is dissolved or dispersed in the aqueous medium.

The product is preferably free from air which can be achieved, for example, by mixing the ingredients in vacuo. The absence of air enables a gel of controlled density to be produced and the keeping properties of the composition to be improved through the incorporation of a minimum of oxygen.

EXAMPLES

The invention is illustrated by the following Examples in which parts and percentages are by weight, unless otherwise indicated.

EXAMPLE 1

0.2 kg dextromethorphan hydrobromide and then 1.6 kg beta-cyclodextrin are added with rapid stirring to 84.09 kg distilled water at 60° C. After cooling to 20° C., 10 kg glycerol and then 0.15 kg aspartame, 0.2 kg sodium benzoate, 0.15 kg citric acid to establish a pH of 4 to 4.5, 0.2 kg banana flavouring and 0.01 kg red colourant are successively added to the solution with stirring, care being taken to dissolve each component before addition of the following component. The mixing operations are carried out in a reactor previously placed under a vacuum. 2.5 kg xanthan gum in the form of granules are then added to the syrup obtained with slow stirring. The gel syrup obtained is then packed in 75 ml cylindrical plastic dispenser packs incorporating a metering pump (VARIO-DISPENSER) which are arranged upside down and which are then closed with a plunger serving as base after the filled cylinder has been degassed.

By applying pressure to the distributor head, an exact dose of 2 ml of gel syrup is dispensed into a spoon which can be turned over without the product running.

EXAMPLES 2 to 9

Gel syrups having the composition shown in Table I below are prepared in the same way as described in Example 1.

In some cases only, the active principle is adsorbed onto beta-cyclodextrin (Examples 4,5,6 and 7).

In Example 9, the active principle is contacted with magnesium trisilicate as a micronized, porous solid adsorbate.

The composition of the gel syrups is shown in Table II below:

TABLE II

| Example % | 10 | 11 | 12 |
|---|---|---|---|
| Paracetamol | 3 | 6 | 12.5* |
| Hydroxyethyl cellulose | 2 | 2 | 2 |
| Silicate of magnesium and aluminium | 1 | 1 | 1 |
| Glycerol | 15 | 15 | 15 |
| Sorbitol | 15 | 15 | 15 |
| Methyl parabene | 0.15 | 0.15 | 0.15 |
| Sodium saccharinate | 0.1 | 0.1 | 0.1 |
| Monoammonium glycyrrhizinate | 0.03 | 0.03 | 0.03 |
| Sodium or calcium cyclamate | 0.03 | 0.03 | 0.03 |
| Apricot flavouring | 0.35 | 0.35 | 0.35 |
| Colourant | d.q. | d.q. | d.q. |
| Water | q.s.f | q.s.f | q.s.f |

Legend:
* = In Example 12, the paracetamol is in the form of a powder coated in a fluidized bed, the % indicated relating to the active principle
d.q. = Desired quantity
q.s.f = Balance to 100

TABLE I

| Example % | 2 | 3 | 4 | 5 | 6 | 7 | 8 | 9 |
|---|---|---|---|---|---|---|---|---|
| Dextromethorphan hydrobromide | 0.2 | 0.2 | 0.2 | 0.2 | 0.2 | 0.4 | 0.2 | 2 |
| Beta-cyclodextrin | — | — | 1.6 | 1.6 | 1.6 | 3.6 | — | — |
| Solid adsorbate, micronized | — | — | — | — | — | — | — | 18 |
| Sucrose | 30 | 30 | — | — | — | — | 30 | — |
| Glycerol | — | — | 10 | 10 | 10 | — | — | — |
| Monoammonium glycyrrhizinate | 0.1 | 0.1 | — | — | — | — | 0.1 | — |
| Aspartame | — | — | 0.15 | 0.15 | 0.15 | 0.15 | — | 0.2 |
| Sodium benzoate | 0.3 | 0.3 | 0.2 | 0.2 | 0.2 | 0.3 | 0.3 | 0.2 |
| Methyl para-benzoate | 0.02 | 0.02 | — | — | — | 0.02 | 0.02 | — |
| Citric acid | — | — | 0.15 | 0.15 | 0.15 | — | — | 0.15 |
| Flavouring | 0.02 Chocolate | 0.02 Strawberry | 0.2 Apricot | 0.2 Strawberry | 0.2 Banana/mint | 0.04 Strawberry | 0.02 Strawberry | 0.2 Strawberry |
| Colourant | — | — | — | — | 0.03 | 0.02 | — | 0.03 |
| Xanthan gum | 2 | 2.2 | 2.5 | 2.5 | 2.5 | 2.5 | 1.9 | 1.5 |
| Hydroxypropyl methyl cellulose | — | — | — | — | — | — | 0.1 | — |
| Water | 67.36 | 67.14 | 85.1 | 85.1 | 84.97 | 91.97 | 67.36 | 77.72 |

All the above gel syrups may be dispensed into a spoon in an exact dose without any of the product running, even when the spoon is turned over.

The above gel syrups have an entirely acceptable appearance, stability and taste. In addition, they may be dispensed in exact doses without running.

EXAMPLES 10–12

Gel syrups are prepared in the same way as in Example 1 using as gelling agent hydroxyethyl cellulose in conjunction with a silicate as flow modifier and using paracetamol as the active principle.

EXAMPLE 13–20

In these Examples, the gel syrups are prepared with dextromethorphan in the same way as described in Example 1, except that the various gelling agents mentioned are used in the proportions shown in Table III below.

TABLE III

| Example % | 13 | 14 | 15 | 16 | 17 | 18 | 19 | 20 |
|---|---|---|---|---|---|---|---|---|
| Dextromethorphan.HBr | 0.78 | 0.78 | 0.78 | 0.78 | 0.78 | 0.78 | 0.78 | 0.78 |
| Beta-cyclodextrin | 12 | 12 | 12 | 12 | 12 | 12 | 12 | 12 |
| Carboxymethyl cellulose | — | — | — | — | — | — | 2 | 1 |
| Hydroxyethyl cellulose | — | 1 | — | — | — | — | — | — |
| Hydroxypropyl cellulose 1 | 2 | — | 2 | — | — | — | — | — |
| Hydroxypropyl cellulose 2 | — | — | — | 2.5 | — | — | — | — |
| Hydroxypropyl methyl cellulose 3 | — | — | — | — | — | 2.5 | — | — |
| Hydroxypropyl methyl cellulose 4 | — | — | — | — | 2.5 | — | — | — |
| Silicate of magnesium and aluminium | 1 | 1 | 1 | 1 | 1 | 1 | 1 | 1 |
| Glycerol | 15 | 15 | 15 | 15 | 15 | 15 | 15 | 15 |
| Sorbitol | 15 | 15 | — | — | — | — | — | — |
| Methyl parabene | 0.15 | 0.15 | 0.15 | 0.15 | 0.15 | 0.15 | 0.15 | 0.15 |
| Sodium saccharinate | 0.1 | 0.1 | 0.1 | 0.1 | 0.1 | 0.1 | 0.1 | 0.1 |
| Monoammonium glycyrrhizinate | 0.03 | 0.03 | 0.03 | 0.03 | 0.03 | 0.03 | 0.03 | 0.03 |
| Sodium or calcium cyclamate | 0.03 | 0.03 | 0.03 | 0.03 | 0.03 | 0.03 | 0.03 | 0.03 |
| Apricot flavouring | 0.35 | 0.35 | 0.35 | 0.35 | 0.35 | 0.35 | 0.35 | 0.35 |
| Colourant | d.q. | d.q. | d.q. | d.q. | d.q. | d.q. | d.q. | d.q |
| Water | q.s.f | q.s.f | q.s.f | q.s.f | q.s.f | q.s.f | q.s.f | q.s.f |

Legend:
1 = Klucel HF ®; 2 = Klucel MF ®; 3 = Methocel K100M Prem. ®; 4 = Methocel 4M ®

The above gel syrups have an entirely acceptable appearance, stability and taste. In addition, they may be dispensed in exact doses without running.

EXAMPLE 21–27

The gel syrups are prepared in the same way as described in Example 1, except that different active principles and different gelling agents are used in the proportions shown in Table IV below.

The above gel syrups have an entirely acceptable appearance, stability and taste. They may be dispensed in exact doses without running.

EXAMPLE 28–41

Gel syrups are prepared in the same way as described in Example 1, the active principles and the gelling agents being used in the proportions shown in Table V below.

TABLE IV

| Example % | 21 | 22 | 23 | 24 | 25 | 26 | 27 |
|---|---|---|---|---|---|---|---|
| Paracetamol | 12.5* | — | — | 12.5* | — | 3 | 2.72 |
| Ibuprofen | — | 10* | — | — | — | — | — |
| Phenyl ephedrine.HCl | — | — | 0.5 | — | — | — | — |
| Chorphenamine "Maleas" | — | — | 0.2 | — | — | — | — |
| Pseudoephedrine.HCl | — | — | — | — | — | — | 0.54 |
| Triprolidine.HCl | — | — | — | — | — | — | 0.03 |
| Dextromethorphan.HBr | — | — | — | — | 0.78 | — | — |
| Beta-cyclodextrin | — | — | — | — | 12 | — | — |
| Hydroxyethyl cellulose | 1.5 | 1.5 | — | — | — | — | — |
| Xanthan gum | — | — | 2.5 | — | — | 2.2 | 2.2 |
| Carbomer 934P | — | — | — | 1 | 1 | — | — |
| Glycerol | 15 | 15 | 15 | 15 | 15 | 10 | 15 |
| Propylene glycol | — | 10 | — | — | — | — | 8.65 |
| Sorbitol | 15 | — | — | 15 | 15 | 15 | 15 |
| Ethanol, 95° | 0.2 | 0.2 | 0.2 | — | — | — | — |
| Sodium benzoate | 0.2 | 0.2 | 0.2 | — | — | — | — |
| Methyl parabene | — | — | — | 0.15 | 0.15 | 0.1 | 0.1 |
| Propyl parabene | — | — | — | — | — | 0.02 | — |
| Sodium saccharinate | 0.2 | 0.2 | 0.2 | 0.2 | 0.2 | 0.1 | 0.2 |
| Monoammonium glycyrrhizinate | 0.08 | 0.08 | 0.09 | 0.08 | 0.08 | — | — |
| Sodium or calcium cyclamate | 0.02 | 0.02 | 0.03 | 0.02 | 0.02 | — | — |
| Apricot flavouring | 0.35 | 0.35 | 0.35 | 0.35 | 0.35 | 0.35 | — |
| Raspberry flavouring | — | — | — | — | — | 0.3 | — |
| Banana/vanilla flavouring | — | — | — | — | — | — | 0.2 |
| Colourant | d.q. | d.q. | d.q. | d.q. | d.q. | d.q. | d.q. |
| Water | q.s.f | q.s.f | q.s.f | q.s.f | q.s.f | q.s.f | q.s.f |

Legend:
* = The paracetamol (Examples 21 and 24) and the ibuprofen (Example 22) are in the form of powders coated in a fluidized bed, the % indicated relating to the active principle.

TABLE V

| Example % | 28 | 29 | 30 | 31 | 32 | 33 | 34 |
|---|---|---|---|---|---|---|---|
| Paracetamol | — | — | — | 3.12* | 3.12* | 12.5* | 6.25* |
| Ibuprofen | — | 6.66* | — | — | — | — | — |
| Dihydroxyaluminium carbonate | 8.75 | — | — | — | — | — | — |
| Aminoacetate | 3.75 | — | — | — | — | — | — |
| Pseudoephedrine.HCl | — | — | 0.75 | 0.63 | 0.63 | — | 0.75 |
| Triprolidine.HCl | — | — | 0.03 | 0.03 | 0.03 | — | — |
| Multivitamin mix | — | — | — | — | — | — | — |
| Guaiphenesin | — | — | — | — | — | — | — |
| Acrivastine | — | — | — | — | — | — | 0.08 |
| Carbocysteine | — | — | — | — | — | — | — |
| Dextromethorphan.HBr | — | — | 0.37 | — | — | — | — |
| Beta-cyclodextrin | — | — | 5.2 | — | — | — | — |
| Xanthan gum | 2.3 | 2.3 | 2.5 | — | — | — | 2.3 |
| Carbomer 934P | — | — | — | 1.7 | — | — | — |
| Methyl cellulose | — | — | — | — | 2.74 | — | — |
| Hydroxypropyl methyl cellulose | — | — | — | — | — | 2.48 | — |
| Glycerol | 15 | 15 | 10 | — | — | — | 15 |
| Propylene glycol | — | 6.66 | — | — | — | — | — |
| Sodium hydroxide | — | — | — | 0.79 | — | — | — |
| Sodium benzoate | 0.2 | 0.2 | 0.2 | 0.2 | 0.2 | 0.2 | 0.2 |
| Sodium saccharinate | 0.2 | 0.2 | 0.15 | 0.2 | 0.2 | 0.2 | 0.2 |
| Monoammonium glycyrrhizinate | 0.03 | 0.03 | 0.03 | 0.03 | 0.03 | 0.03 | 0.3 |
| Sodium or calcium cyclamate | 0.03 | 0.03 | 0.03 | 0.03 | 0.03 | 0.03 | 0.3 |
| Apricot flavouring | 0.35 | 0.35 | 0.35 | 0.35 | 0.35 | 0.35 | 0.35 |
| Colourant | d.q. | d.q. | d.q. | d.q. | d.q. | d.q. | d.q. |
| Water | q.s.f | q.s.f | q.s.f | q.s.f | q.s.f | q.s.f | q.s.f |

| Example % | 35 | 36 | 37 | 38 | 39 | 40 | 41 |
|---|---|---|---|---|---|---|---|
| Paracetamol | — | — | — | — | — | — | — |
| Ibuprofen | — | — | — | 5* | 5* | 5* | — |
| Dihydroxyaluminium carbonate | — | — | — | — | — | — | — |
| Aminoacetate | — | — | — | — | — | — | — |
| Pseudoephedrine.HCl | 0.75 | 0.75 | — | 0.75 | — | — | — |
| Triprolidine.HCl | — | — | 0.03 | — | — | — | — |
| Multivitamin mix | — | — | — | — | — | — | 3.5 |
| Guaifenesin | — | 5 | — | — | — | — | — |
| Acrivastine | 0.08 | 0.08 | — | — | — | — | — |
| Carbocysteine | — | — | — | — | — | 19 | — |
| Dextromethorphan.HBr | 0.37 | — | — | — | — | — | — |
| Beta-cyclodextrin | 5.2 | — | — | — | — | — | — |
| Xanthan gum | 2.3 | 2.3 | 2.3 | 2.3 | 2.3 | 2.3 | 2.3 |
| Carbomer 934P | — | — | — | — | — | — | — |
| Methyl cellulose | — | — | — | — | — | — | — |
| Hydroxypropyl methyl cellulose | — | — | — | — | — | — | — |
| Glycerol | 15 | 15 | 15 | 15 | 15 | 15 | 15 |
| Propylene glycol | — | — | — | — | — | — | — |
| Sodium hydroxide | — | — | — | — | — | — | — |
| Sodium benzoate | 0.2 | 0.2 | 0.2 | 0.2 | 0.2 | 0.2 | 0.2 |
| Sodium saccharinate | 0.2 | 0.2 | 0.2 | 0.2 | 0.2 | 0.2 | 0.2 |
| Monoammonium glycyrrhizinate | 0.03 | 0.03 | 0.03 | 0.03 | 0.03 | 0.03 | 0.03 |
| Sodium or calcium cyclamate | 0.03 | 0.03 | 0.03 | 0.03 | 0.03 | 0.03 | 0.03 |
| Apricot flavouring | 0.35 | 0.35 | 0.35 | 0.35 | 0.35 | 0.35 | 0.35 |
| Colourant | d.q. | d.q. | d.q. | d.q. | d.q. | d.q. | d.q. |
| Water | q.s.f | q.s.f | q.s.f | q.s.f | q.s.f | q.s.f | q.s.f |

Legend:
* = The paracetamol (Examples 31,32,33 and 34) and the ibuprofen (Examples 29,38,39 and 40) are in the form of powders coated in a fluidized bed, the % indicated relating to the active principle.

The above gel syrups have an entirely acceptable appearance, stability and taste. They may be dispensed in exact doses without running.

We claim:

1. A pharmaceutical delivery system comprising:
    an orally administerable pharmaceutical composition comprising an active pharmaceutical principle homogeneously distributed in a water-dispersible gel excipient containing an acrylamide or acrylamidine gelling agent, the gelling agent being present in the composition in an amount of from 0.2% to 5% by weight based upon the weight of the composition; and
    a dispenser pack which contains the composition in an amount sufficient for at least 5 days of therapeutic treatment and which has an internal volume of from 20 ml to 150 ml, a metering compartment not exceeding 5 ml in volume and a metering pump suitable for dispensing, in up to two depressions, a therapeutic dose of the composition.

2. A system according to claim 1 wherein the active principle is encapsulated.

3. A system according to claim 1 wherein the active principle is encapsulated in an encapsulating system selected from the group consisting of an open newtonian system, a closed newtonian matrix system, an open brownian system, a closed brownian matrix system and a vesicular system.

4. A system according to claim 1 wherein the active principle is encapsulated in an encapsulating system selected from the group consisting of microsponges, microspheres, microcapsules, nanocapsules, liposomes and beta-cyclodextrin.

5. A system according to claim 1 wherein the composition further comprises a lipid in which the principle is solubilized and which is dispersed as droplets in the gel excipient.

6. A system according to claim 1 wherein the composition further comprises glycerol.

7. A system according to claim 1 wherein the composition further comprises a preservative, a flavoring, a sweetening agent and a colorant.

8. A system according to claim 1 wherein the active principle is selected from the group consisting of antacids, antidiarrhoeics, antihistaminics, anti-emetics, antitussives, anti-inflammatories, analgesics/antipyretics, bronchial mucomodifiers, antispasmodics, respiratory analeptics/antihistaminics, systemic alpha-sympathomimetics, laxatives and vitamin complexes.

9. A system according to claim 1 further comprising a pressure activated plunger connected to the metering pump for drawing a dose of the composition.

10. A system according to claim 1 further comprising a flexible membrane in a form of a finger positioned within the pack to contain the composition, and a propellant gas contained within the pack about the membrane for applying pressure to the membrane.

11. A process for preparing a packaged, orally administerable, pharmaceutical composition comprising adding a gelling agent to an aqueous medium containing an active pharmaceutical principle and stirring to form a gelled composition and then packing the composition in a dispenser pack having a metering pump for dispensing metered doses of the composition, wherein the gelling agent is an acrylamide or acrylamidine and is present in the composition in an amount of from 0.2% to 5% by weight based upon the weight of the composition.

12. A process according to claim 11 further comprising adding and mixing the active principle and water to form the aqueous medium in vacuo.

13. A process according to claim 11 further comprising mixing a preservative, a flavouring, a sweetening agent and a colorant with the active principle and water to form the aqueous medium.

14. A process according to claim 13 wherein the mixing is in vacuo.

15. A process according to claim 11 wherein the active principle is dissolved in the aqueous medium.

16. A process according to claim 11 wherein the active principle is dispersed in the aqueous medium.

17. A process according to claim 11 further comprising first encapsulating the active principle and then dispersing the encapsulated active principle in the aqueous medium.

* * * * *